(12) United States Patent
Qian et al.

(10) Patent No.: US 12,161,860 B2
(45) Date of Patent: Dec. 10, 2024

(54) GRAPHENE COCHLEAR IMPLANT ELECTRODE AND MANUFACTURING METHOD THEREOF

(71) Applicants: ZHEJIANG NUROTRON BIOTECHNOLOGY CO., LTD., Hangzhou (CN); NANJING DRUM TOWER HOSPITAL, Nanjing (CN)

(72) Inventors: Xiaoyun Qian, Nanjing (CN); Shuqi Qi, Hangzhou (CN); Xia Gao, Nanjing (CN); Xiaoan Sun, Hangzhou (CN); Renjie Chai, Nanjing (CN)

(73) Assignees: ZHEJIANG NUROTRON BIOTECHNOLOGY CO., LTD., Hangzhou (CN); NANJING DRUM TOWER HOSPITAL, Nanjing (CN)

( * ) Notice: Subject to any disclaimer, the term of this patent is extended or adjusted under 35 U.S.C. 154(b) by 377 days.

(21) Appl. No.: 17/627,713

(22) PCT Filed: Aug. 23, 2019

(86) PCT No.: PCT/CN2019/102227
§ 371 (c)(1),
(2) Date: Jan. 17, 2022

(87) PCT Pub. No.: WO2021/007922
PCT Pub. Date: Jan. 21, 2021

(65) Prior Publication Data
US 2022/0226639 A1 Jul. 21, 2022

(30) Foreign Application Priority Data
Jul. 17, 2019 (CN) .......................... 201910643842.1

(51) Int. Cl.
*A61N 1/05* (2006.01)
*A61N 1/36* (2006.01)

(52) U.S. Cl.
CPC ....... *A61N 1/0541* (2013.01); *A61N 1/36038* (2017.08); *H04R 2225/67* (2013.01)

(58) Field of Classification Search
CPC .............. A61N 1/0541; A61N 1/36038; H04R 2225/67
See application file for complete search history.

(56) References Cited

U.S. PATENT DOCUMENTS

| 5,000,194 A | * | 3/1991 | van den Honert | ... A61N 1/0541 607/137 |
| 2005/0234535 A1 | * | 10/2005 | Risi | ..................... A61N 1/0541 607/57 |

(Continued)

FOREIGN PATENT DOCUMENTS

| CN | 102583339 | 7/2012 |
| CN | 108421159 | 8/2018 |

(Continued)

OTHER PUBLICATIONS

English translation of CN 109231192 (Year: 2019).*
English translation of CN 108837301 (Year: 2018).*

*Primary Examiner* — Catherine M Voorhees
(74) *Attorney, Agent, or Firm* — Jiwen Chen; Joywin IP Law PLLC

(57) ABSTRACT

The present invention discloses a graphene cochlear implant electrode and a fabrication method thereof. The electrode comprises a tip portion, bendable portions, contact electrodes, an electrode carrier and wire electrodes, wherein the tip portion is disposed at forepart of the cochlear implant electrode, the electrode carrier wraps the wire electrodes and half wraps the contact electrodes connected to the wire electrodes one by one, and each bendable portion is an annular groove disposed on the electrode carrier; each contact electrode comprises an inner contact and an outer contact, when bending, the inner contact faces the modiolus while the outer contact faces away from the modiolus; and each wire electrode is wavy. According to the present invention, the graphene cochlear implant electrode enhances the surface bioactivity of the contact electrodes to facilitate cell adhesion, proliferation and differentiation, while promoting its formation and integration with peripheral nerves as an implant material, thus improving the surface bioactivity and biocompatibility of the contact electrodes of a cochlear implant.

6 Claims, 5 Drawing Sheets

(56) References Cited

U.S. PATENT DOCUMENTS

| | | | | |
|---|---|---|---|---|
| 2007/0088335 A1* | 4/2007 | Jolly | .................... | A61N 1/0541 |
| | | | | 604/891.1 |
| 2015/0283555 A1* | 10/2015 | Khe | ...................... | B82Y 30/00 |
| | | | | 204/547 |
| 2017/0181669 A1* | 6/2017 | Lin | ........................ | G01N 33/66 |
| 2018/0056057 A1* | 3/2018 | Kalita | .................. | A61N 1/0492 |
| 2019/0143100 A1* | 5/2019 | Tourrel | .................. | H05K 1/118 |
| | | | | 607/137 |
| 2021/0038773 A1* | 2/2021 | Cui | ........................ | A61B 5/268 |

FOREIGN PATENT DOCUMENTS

| | | | | |
|---|---|---|---|---|
| CN | 108837301 | | 11/2018 | |
| CN | 108837301 A | * 11/2018 | ........... | A61N 1/0541 |
| CN | 109231192 A | * 1/2019 | ........... | C01B 32/186 |
| CN | 109350847 | | 2/2019 | |

* cited by examiner

GRAPHENE COCHLEAR IMPLANT ELECTRODE AND MANUFACTURING METHOD THEREOF

This is a U.S. national stage application of PCT Application No. PCT/CN2019/102227 under 35 U.S.C. 371, filed Aug. 23, 2019 in Chinese, claiming priority of Chinese Application No. 201910643842.1, filed Jul. 17, 2019, all of which is hereby incorporated by reference.

TECHNICAL FIELD OF THE INVENTION

The present invention relates to the field of electronic medicine, in particular to a graphene cochlear implant electrode and a fabrication method thereof.

BACKGROUND OF THE INVENTION

In recent years, the development of novel bioactive nano-coating materials as intelligent interfaces for cell research and regenerative medicine has been rapidly developing in the field of surface engineering research in biomedicine. The development of nano-coatings on biomaterial surfaces is a demanding field in terms of tissue regeneration, from signal transduction level to macroscopic tissue regeneration. Current research in this field mainly focuses on enhancing surface bioactivity, promoting cell adhesion, migration, proliferation and differentiation on the surface of biomaterials and further enhancing tissue regeneration and, most importantly, being able to be applied to practical clinical work. Many scholars have demonstrated that cell shape, morphology, adhesion, proliferation, migration and differentiation can be controlled by cell-material surface interactions. The relevant factors regulating the cellular behavior of biomaterials are not limited to substrate stiffness, surface morphology or roughness. The density and distribution of adhesive ligands, and the elasticity and chemical properties of the substrate may also cause the up-regulation of neurogenic, myogenic and osteogenic markers in human mesenchymal stem cells (MSCs). Graphene has recently received more attention as a bioactive material in the search for new coating materials that may affect cell behavior.

Graphene is a single layer of carbon atoms arranged in a 2D hexagonal structure with extraordinary electrical, thermal and physical properties. The molecular structure of graphene can be chemically modified by activating different molecular attachments. Although graphene and its derivatives have been widely used in industry and electronics, their application in biomedicine is still at an early stage. The strategy developed so far for the application of graphene to surface engineering and cell differentiation is to use graphene-based materials as cell culture substrates or coated nanomaterials for in vitro stem cell culture to extensively regulate stem cell behavior. This is because graphene substrates can provide a unique physical framework for stem cells comparable to natural extracellular matrix (ECM). Graphene can improve the performance of many devices and can also serve as an "arbitrary-shaped" monolayer scaffold with good biocompatibility to enhance stem cell differentiation. In particular, graphene and its derivatives have relatively low biotoxicity and high loading capacity in addition to good biocompatibility, making them effective carriers for a variety of bioactive factors such as proteins. These excellent properties and potential applications of graphene have fostered the development of composites, including few-layer graphene (FLG), ultrathin graphite, graphene oxide (GO), reduced graphene oxide (rGO), and graphene-based functional nanocomposites (GNS), forming a complete set of "graphene family nanocomposites" (GFNs). Some of these composites, such as graphene oxide (GO), have been shown to stimulate the differentiation of human mesenchymal stem cells (MSCs) into adipocytes and myoblasts, and induce neural stem cells (NSCs) into neurons and pluripotent stem cells into endodermal cell lineages.

SUMMARY OF THE INVENTION

A technical problem to be solved by the present invention is to provide a graphene cochlear implant electrode, which enhances the surface bioactivity of the contact electrodes to facilitate cell adhesion, proliferation and differentiation, while promoting its formation and integration with peripheral nerves as an implant material, thus improving the surface bioactivity and biocompatibility of the contact electrodes of a cochlear implant.

For this object, a technical solution employed in the present invention is as follows. A graphene cochlear implant electrode is provided, comprising a tip portion, bendable portions, contact electrodes, an electrode carrier and wire electrodes, wherein the tip portion is disposed at a forepart of the cochlear implant electrode, the electrode carrier wraps the wire electrodes and half wraps the contact electrodes connected to the wire electrodes one by one, and each bendable portion is an annular groove disposed on the electrode carrier; each contact electrode comprises an inner contact and an outer contact, when bending, the inner contact faces the modiolus while the outer contact faces away from the modiolus; and each wire electrode is in a wavy shape.

Preferably, the electrode carrier is made of graphene oxide-grafted silica gel.

Preferably, the inner contact is a graphene-coated metal sheet.

Preferably, the outer contact is a sheet with graphene growing from porous metal.

For this object, a fabrication or manufacturing method of the graphene cochlear implant electrode is further provided in the present invention, comprising the following steps of:

S10, fabricating contact electrodes into a sheet shape by high-pressure annealing, rolling, laser cutting and punch forming;

S20, fabricating wire electrodes by annealing, cold drawing and straightening platinum-iridium alloy billets into platinum-iridium alloy wires; machining the platinum-iridium alloy wires to be wavy to obtain the wire electrodes; and welding the contact electrodes to the wire electrodes, and performing ultrasonic cleaning and plasma treatment;

S30, wrapping an electrode carrier: after the contact electrodes and the wire electrodes are arranged in place, performing injection molding to form annular grooves on the electrode carrier; and S40, performing laser cutting, cleaning and electrical inspection on exposed surfaces of the contact electrodes.

Preferably, each contact electrode comprises an inner contact and an outer contact.

Preferably, the inner contact is fabricated by following steps of:

S11, adhering a copper substrate graphene sheet on a main tray of a spin-coating centrifuge, evenly applying 7% PMMA to a surface of the copper substrate graphene sheet with a pipette, adjusting the speed of the spin-coating centrifuge to 3,000 r/min for coating the sheet by spinning for 10 seconds to 20 seconds, and putting the coated sheet into a vacuum oven at 150° C. for 15 min of solidification;

S12, dissolving the copper substrate graphene sheet coated with PMMA in 1 mol/L ferric chloride solution for 12 hours to 24 hours until copper is chemically eroded by iron ions in ferric chloride, leaving a composite film of PMMA and graphene;

S13, transferring the obtained composite film with a glass slide to deionized water to clean the residual ferric chloride solution;

S14, transferring the composite film by physical adsorption to a surface of a selected metal sheet, and drying the composite film in an oven at 60° C. after naturally drying for 12 hours to 24 hours;

S15, dissolving the dried composite film which is a PMMA/graphene/metal sheet composite in acetone for 24 hours to 48 hours until PMMA is completely dissolved to obtain a graphene-modified metal sheet; and S16, ultrasonically cleaning the graphene-modified metal sheet with absolute ethyl alcohol and deionized water in turn three times for 5 min each time, and drying the sheet in the oven at 60° C. to obtain a graphene-coated metal sheet.

Preferably, the outer contact is fabricated by following steps of:

S121, cutting porous metal taken as a growth substrate for graphene into a sheet of 20 mm*20 mm, and putting the sheet into a quartz tube with an outer diameter of 25 mm and an inner diameter of 22 mm;

S122, heating the porous metal to 1,000° C. and annealing for 5 min in a horizontal tubular furnace in the presence of argon at a flow rate of 500 sccm and hydrogen at a flow rate of 200 sccm to clean its surface and remove an oxide layer from its surface;

S123, introducing small amounts of methane at flow rates of 2 sccm, 3.5 sccm, 5 sccm, 7 sccm and 10 sccm into reaction tubes under ambient pressure, respectively, to form concentrations of 0.3 vol %, 0.5 vol %, 0.7 vol %, 1.0 vol % and 1.4 vol % in the total gas flow; and S124, stopping methane after flowing in the reaction gas mixture for 5 min and cooling to room temperature at a rate of 100° C./min in the presence of argon at a flow rate of 500 sccm and hydrogen at a flow rate of 200 sccm.

The graphene cochlear implant electrode employing the above technical solution at least has following beneficial effects.

1. Graphene enhances the surface bioactivity of the contact electrodes to facilitate cell adhesion, proliferation and differentiation, while promoting its formation and integration with peripheral nerves as an implant material, thus improving the surface bioactivity and biocompatibility of the contact electrodes of a cochlear implant.

2. The contact electrodes include inner contacts and outer contacts. Compared with cochlear implant electrodes with a single row of contact electrodes in the prior art, the staggered contact electrodes can be implanted without considering the orientation of electrode contacts, and after the electrode is implanted, the active contact in each pair of electrodes can be selected for stimulation. The inner contact is more biocompatible and active, while the outer contact is better in mechanical toughness, so the two contacts can work together to produce better results, and can also be flexibly interchanged to change the structure composition.

3. The design of the bendable portion allows the electrode to be inserted into the cochlea with minimal pressure on the cochlear wall, especially minimal damage to the tympanic structures at the turns, thus preserving the patient's residual hearing to the greatest extent and avoiding damage to the fine structures. When resistance is encountered during insertion, the bendable portions on the electrode carrier will guide the electrode to turn along with the cochlear canal structure to reduce the resistance during insertion.

4. The electrode carrier is made of graphene oxide-grafted silica gel, which improves the hydrophilicity of the silica gel and gives it antibacterial properties while reducing its cytotoxicity, making the cochlear implant electrode much more antibacterial, reliable and safe, ensuring the long-term normal operation of the implanted electrode in the human body and promoting the cochlear implant fabrication technology.

DETAILED DESCRIPTION OF THE INVENTION

Figure 1:
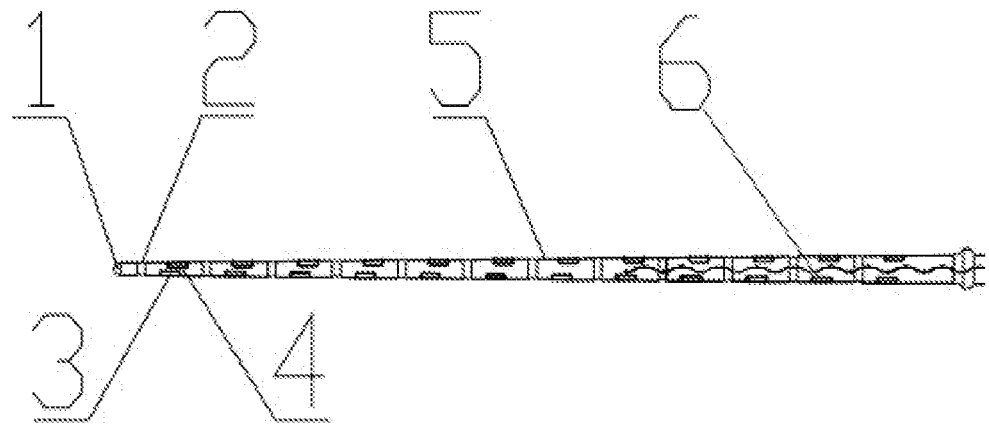
FIG. 1 is a structural diagram of a graphene cochlear implant electrode according to an embodiment of the present invention.
Figure 2:
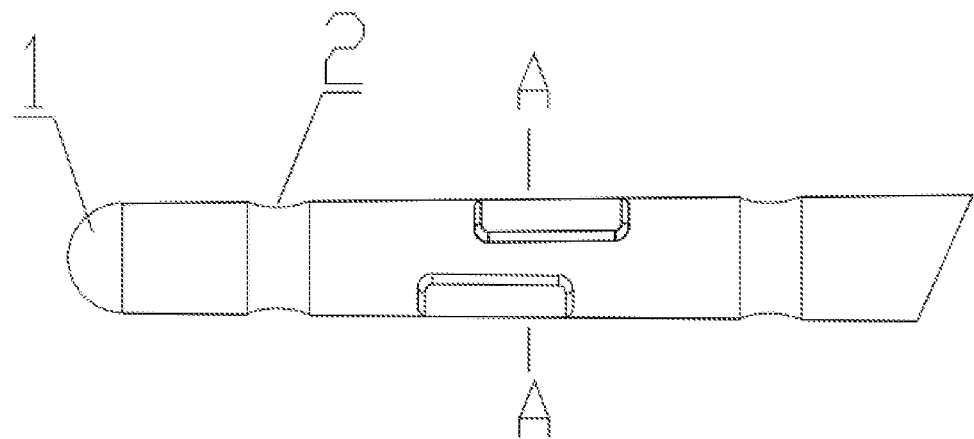
FIG. 2 is an enlarged view of a tip portion in FIG. 1.
Figure 3:
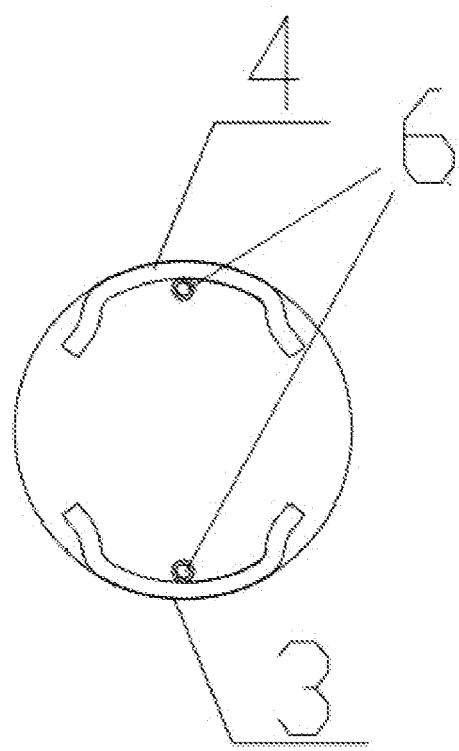
FIG. 3 is a sectional view in a direction A-A in FIG. 2.

As shown in FIGS. 1 to 3, a graphene cochlear implant electrode is provided, including a tip portion 1, bendable portions 2, contact electrodes, an electrode carrier 5 and wire electrodes 6.

The tip portion 1 is disposed at forepart of the cochlear implant electrode, the electrode carrier 5 wraps the wire electrodes 6 and half wraps the contact electrodes connected to the wire electrodes 6 one by one, and each bendable portion 2 is an annular groove disposed on the electrode carrier 5. Each contact electrode includes an inner contact 3 and an outer contact 4, when bending, the inner contact 3 faces the modiolus while the outer contact 4 faces away from the modiolus. Each wire electrode 6 is in a wavy shape.

In one embodiment, the electrode carrier 5 is made of graphene oxide-grafted silica gel.

The inner contact 3 is a graphene-coated metal sheet, and the outer contact 4 is a sheet with graphene growing from porous metal.

Figure 4:
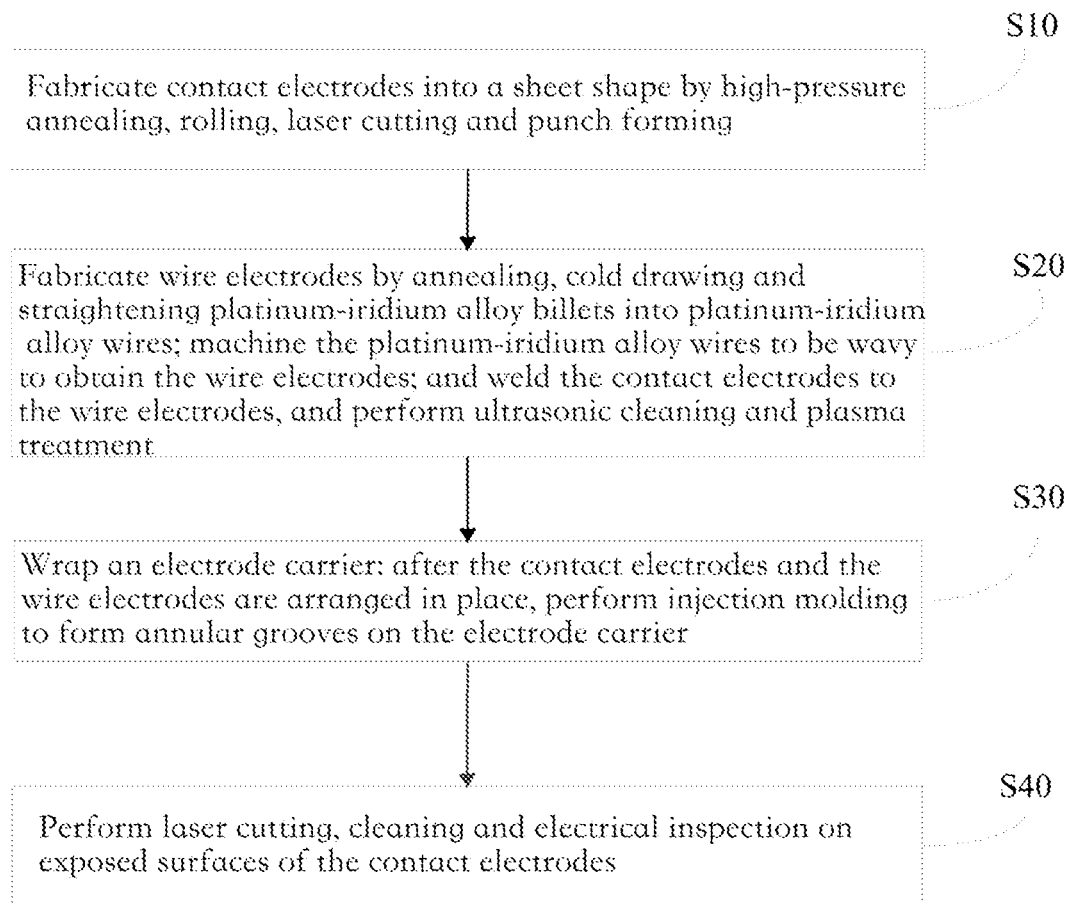
FIG. 4 is a flow chart of a fabrication method of the graphene cochlear implant electrode according to the embodiment of the present invention.
Figure 5:
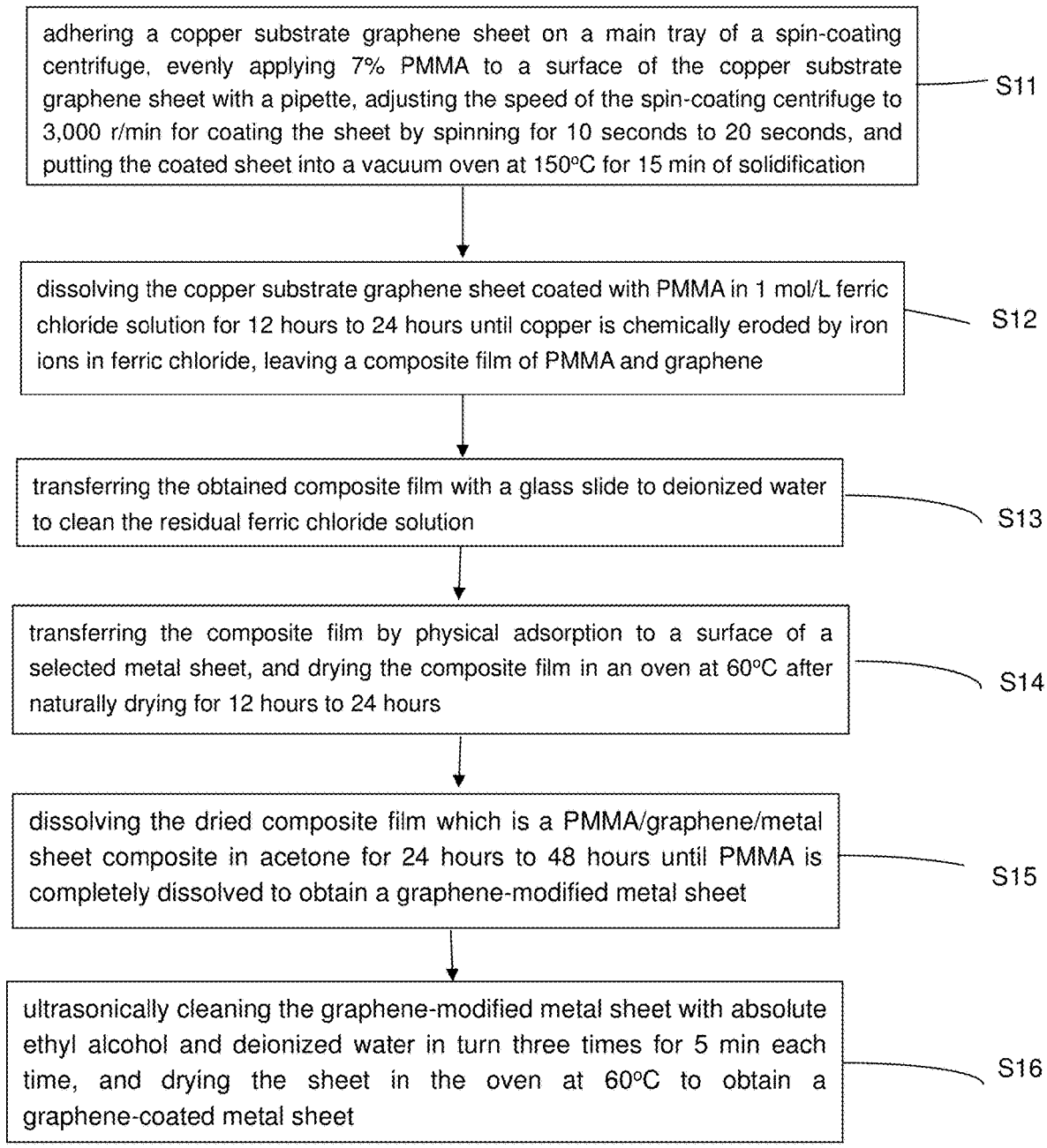
FIG. 5 is a flow chart of a fabrication method for the inner contact of the graphene cochlear implant electrode according to the embodiment of the present invention.
Figure 6:
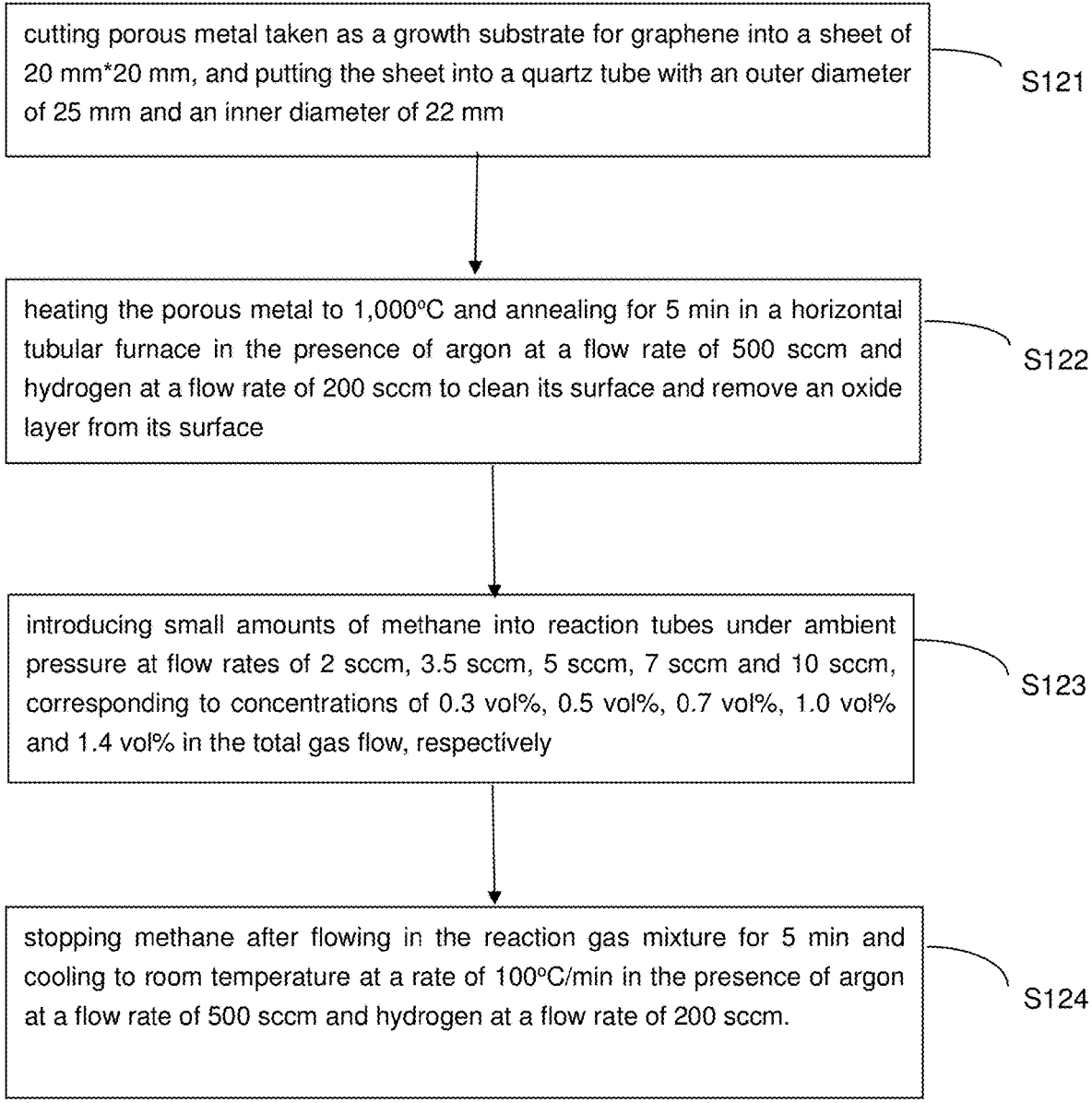
FIG. 6 is a flow chart of a fabrication method for the outer contact of the graphene cochlear implant electrode according to the embodiment of the present invention.

As shown in FIG. 4, a fabrication method of the graphene cochlear implant electrode is provided in an embodiment, including following steps.

In a step of S10, contact electrodes are fabricated into a sheet shape by high-pressure annealing, rolling, laser cutting and punch forming.

In a step of S20, wire electrodes are fabricated by annealing, cold drawing and straightening platinum-iridium alloy billets into platinum-iridium alloy wires; the platinum-iridium alloy wires are machined to be wavy to obtain the wire electrodes; and the contact electrodes are welded to the wire electrodes and subject to ultrasonic cleaning and plasma treatment.

In a step of S30, an electrode carrier is wrapped: after the contact electrodes and the wire electrodes are arranged in place, injection molding is performed to form annular grooves on the electrode carrier.

In a step of S40, laser cutting, cleaning and electrical inspection are performed on exposed surfaces of the contact electrodes.

In one embodiment, each contact electrode includes an inner contact and an outer contact.

The inner contact is fabricated by following steps.

In a step of S11, a copper substrate graphene sheet is adhered on a main tray of a spin-coating centrifuge, 7% PMMA is evenly applied to a surface of the copper substrate graphene sheet with a pipette, the speed of the spin-coating centrifuge is adjusted to 3,000 r/min for coating the sheet by spinning for 10 seconds to 20 seconds, and the sheet is put into a vacuum oven at 150° C. for 15 min of solidification.

In a step of S12, the copper substrate graphene sheet coated with PMMA is dissolved in 1 mol/L ferric chloride solution for 12 hours to 24 hours until copper is chemically eroded by iron ions in ferric chloride, leaving a composite film of PMMA and graphene.

In a step of S13, the obtained composite film is transferred with a glass slide to deionized water to clean the residual ferric chloride solution.

In a step of S14, the composite film is transferred by physical adsorption to a surface of a selected metal sheet, naturally dried for 12 hours to 24 hours, and dried in an oven at 60° C.

In a step of S15, the dried composite film which is a PMMA/graphene/metal sheet composite is dissolved in acetone for 24 hours to 48 hours until PMMA is completely dissolved to obtain a graphene-modified metal sheet.

In a step of S16, the graphene-modified metal sheet is ultrasonically cleaned with absolute ethyl alcohol and deionized water in turn three times for 5 min each time, and dried in the oven at 60° C. to obtain a graphene-coated metal sheet.

Graphene has the potential to be a nano-coating material that binds tightly to a wide variety of metals such as platinum, gold, iridium, titanium and alloys. The graphene coating can significantly improve the surface roughness and hydrophilicity of a substrate material, and only modifies the function of a surface of a metal sheet without significant effect on the overall mechanical properties of the metal sheet. Graphene enhances the surface bioactivity of the metal sheet and significantly promotes the adhesion and proliferation of stem cells.

The outer contact is fabricated by following steps.

In a step of S121, porous metal taken as a growth substrate for graphene is cut into a sheet of 20 mm*20 mm, and put into a quartz tube with an outer diameter of 25 mm and an inner diameter of 22 mm.

In a step of S122, the porous metal is heated to 1,000° C. and annealed for 5 min in a horizontal tubular furnace in the presence of argon at a flow rate of 500 sccm and hydrogen at a flow rate of 200 sccm to clean its surface and remove an oxide layer from its surface.

In a step of S123, small amounts of methane are introduced at flow rates of 2 sccm, 3.5 sccm, 5 sccm, 7 sccm and 10 sccm into reaction tubes under ambient pressure, respectively, to form concentrations of 0.3 vol %, 0.5 vol %, 0.7 vol %, 1.0 vol % and 1.4 vol % in the total gas flow.

In a step of S124, after flowing in the reaction gas mixture for 5 min, methane is stopped and cooled to room temperature at a rate of 100° C./min in the presence of argon at a flow rate of 500 sccm and hydrogen at a flow rate of 200 sccm.

The sheet with graphene growing from porous metal integrates the unique morphology characteristics of a 3D network and the unique physicochemical properties of graphene. It has extremely low density, extremely high porosity and high specific surface area, as well as excellent electrical, thermal and mechanical properties of graphene, such as reblending flexible polymers such as silica gel and silk protein, and can remove porous metals by chemical methods, leaving only polymers of graphene and silica gel, thus forming a graphene flexible network with more excellent electrical and mechanical properties.

Finally, it should be noted that the above preferred embodiments are not used for limiting but merely for describing the technical solutions of the present invention. Although the present invention has been described in detail by the above preferred embodiments, it should be understood by those of skill in the art that various modifications may be made thereto in form and detail without deviating from the scope defined by the claims of the present invention.

The invention claimed is:

1. A graphene cochlear implant electrode array, comprising a tip portion, bendable portions, contact electrodes, an electrode carrier and wire electrodes, wherein
   the tip portion is disposed at a forepart of the cochlear implant electrode array, the electrode carrier wraps around the wire electrodes, and wraps around the contact electrodes except for exposed surfaces of the contact electrodes, wherein the contact electrodes are connected to the wire electrodes one by one, and each bendable portion is an annular groove disposed on the electrode carrier; each contact electrode comprises an inner contact and an outer contact, when bending, the inner contact faces the modiolus while the outer contact faces away from the modiolus; and each wire electrode is in a wavy shape;
   wherein the electrode carrier is made of graphene oxide-grafted silica gel.

2. The graphene cochlear implant electrode array according to claim 1, wherein the inner contact is a graphene-coated metal sheet.

3. The graphene cochlear implant electrode array according to claim 1, wherein the outer contact is a sheet with graphene growing from porous metal.

4. A fabrication method of the graphene cochlear implant electrode array according to claim 1, comprising the following steps:
   (S10) fabricating contact electrodes into a sheet shape by high-pressure annealing, rolling, laser cutting and punch forming;
   (S20) fabricating wire electrodes by annealing, cold drawing and straightening platinum-iridium alloy billets into platinum-iridium alloy wires; machining the platinum-iridium alloy wires to be wavy to obtain the wire electrodes; and welding the contact electrodes to the wire electrodes, and performing ultrasonic cleaning and plasma treatment;
   (S30) wrapping the electrode carrier around the contact electrodes and the wire electrodes: after the contact electrodes and the wire electrodes are arranged in place, performing injection molding of the electrode carrier to wrap around the contact electrodes and the wire electrodes, and to form annular grooves on the electrode carrier; and (S40) performing laser cutting, cleaning and electrical inspection on the exposed surfaces of the contact electrodes.

5. The fabrication method of graphene cochlear implant electrode array according to claim 4, wherein the inner contact is fabricated by following steps of:
- (S11) adhering a copper substrate graphene sheet on a main tray of a spin-coating centrifuge, evenly applying 7% poly(methyl methacrylate) (PMMA) to a surface of the copper substrate graphene sheet with a pipette, adjusting the speed of the spin-coating centrifuge to 3,000 r/min for coating the sheet by spinning for 10 seconds to 20 seconds, and putting the coated sheet into a vacuum oven at 150° C. for 15 min of solidification;
- (S12) dissolving the copper substrate graphene sheet coated with PMMA in 1 mol/L ferric chloride solution for 12 hours to 24 hours until copper is chemically eroded by iron ions in ferric chloride, leaving a composite film of PMMA and graphene;
- (S13) transferring the obtained composite film with a glass slide to deionized water to clean the residual ferric chloride solution;
- (S14) transferring the composite film by physical adsorption to a surface of a selected metal sheet, and drying the composite film in an oven at 60° C. after naturally drying for 12 hours to 24 hours;
- (S15) dissolving the dried composite film which is a PMMA/graphene/metal sheet composite in acetone for 24 hours to 48 hours until PMMA is completely dissolved to obtain a graphene-modified metal sheet; and
- (S16) ultrasonically cleaning the graphene-modified metal sheet with absolute ethyl alcohol and deionized water in turn three times for 5 min each time, and drying the sheet in the oven at 60° C. to obtain a graphene-coated metal sheet.

6. The fabrication method of the graphene cochlear implant electrode array according to claim 4, wherein the outer contact is fabricated by following steps of:
- (S121) cutting porous metal taken as a growth substrate for graphene into a sheet of 20 mm*20 mm, and putting the sheet into a quartz tube with an outer diameter of 25 mm and an inner diameter of 22 mm;
- (S122) heating the porous metal to 1,000° C. and annealing for 5 min in a horizontal tubular furnace in the presence of argon at a flow rate of 500 sccm and hydrogen at a flow rate of 200 sccm to clean its surface and remove an oxide layer from its surface;
- (S123) introducing small amounts of methane into reaction tubes under ambient pressure at flow rates of 2 sccm, 3.5 sccm, 5 sccm, 7 sccm and 10 sccm, corresponding to concentrations of 0.3 vol %, 0.5 vol %, 0.7 vol %, 1.0 vol % and 1.4 vol % in the total gas flow, respectively; and
- (S124) stopping methane after flowing in the reaction gas mixture for 5 min and cooling to room temperature at a rate of 100° C./min in the presence of argon at a flow rate of 500 sccm and hydrogen at a flow rate of 200 sccm.

\* \* \* \* \*